United States Patent [19]

Slemmer et al.

[11] Patent Number: 4,694,825
[45] Date of Patent: Sep. 22, 1987

[54] CONTROL FOR RESPIRATORS

[75] Inventors: Janos Slemmer, Gross Grönau; Gottfried Schröter, Lübeck, both of Fed. Rep. of Germany

[73] Assignee: Drägerwerk AG, Fed. Rep. of Germany

[21] Appl. No.: 672,275

[22] Filed: Nov. 16, 1984

[30] Foreign Application Priority Data

Nov. 18, 1983 [DE] Fed. Rep. of Germany ....... 3341711

[51] Int. Cl.$^4$ ............................................ A61M 16/00
[52] U.S. Cl. .............................. 128/205.24; 137/494; 251/333
[58] Field of Search ......... 128/205.24, 203.12–203.14, 128/203.22–203.23, 204.18, 204.26; 137/494, 528; 251/61, 61.1, 64, 333

[56] References Cited

U.S. PATENT DOCUMENTS

| 3,519,012 | 7/1970 | Van Patten | 137/860 X |
| 3,726,274 | 4/1973 | Bird et al. | 128/205.24 |
| 3,826,255 | 7/1974 | Haustad et al. | 128/200.18 |
| 3,850,197 | 11/1974 | Ernst | 128/205.24 |
| 3,942,547 | 3/1976 | Pfitzner | 128/205.24 X |
| 4,180,066 | 12/1979 | Milliken et al. | 128/205.24 |
| 4,190,045 | 2/1980 | Bartels | 128/205.24 |
| 4,239,038 | 12/1980 | Holmes | 128/205.13 |
| 4,316,458 | 2/1982 | Hammerton-Fraser | 128/205.24 |
| 4,331,140 | 5/1982 | Hallsey | 128/205.24 X |
| 4,454,893 | 6/1984 | Orchard | 128/205.24 X |

FOREIGN PATENT DOCUMENTS 0185702 10/1966 U.S.S.R. .......... 128/205.24

Primary Examiner—Kyle L. Howell
Assistant Examiner—Angela D. Sykes
Attorney, Agent, or Firm—McGlew and Tuttle

[57] ABSTRACT

A control for use by a patient who is connected with a respirator comprises a valve housing which has an interior valve chamber with a gas inlet extending into the chamber and terminating at an annular valve seat which is closable by a diaphragm. A gas outlet is also connected into the valve chamber. The valve housing also has a control chamber in the opposite side of the diaphragm from the valve chamber and an inhaling gas supply connection extends into the control chamber. In addition a gas take-off conduit connectable to the patient is connected into the control chamber. The gas take-off is provided with an orifice plate which defines a reduced area in the take-off so that during use by the patient during inhaling a pressure lower or higher than the pressure in the valve chamber is produced in the control chamber and opening or closing of the diaphragm end valve is effected to permit or prevent exhaled gas to pass through the gas inlet connection to the valve chamber and then to the gas outlet.

3 Claims, 1 Drawing Figure

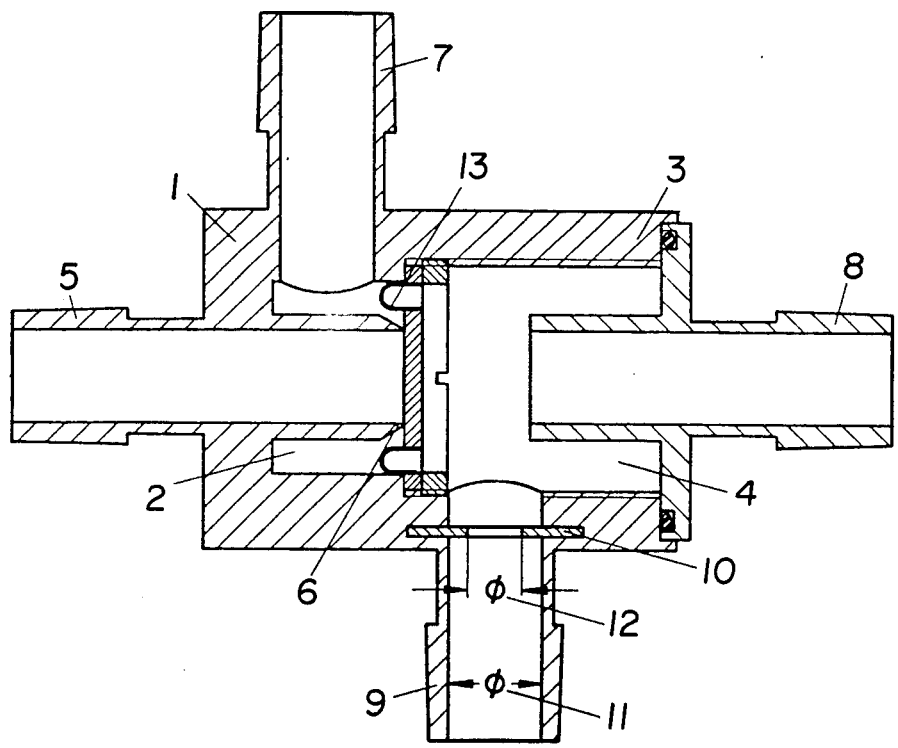

CONTROL FOR RESPIRATORS

FIELD AND BACKGROUND OF THE INVENTION

This invention relates in general to the construction of control devices for respirators and in particular to a new and useful control for respirators including a controllable diaphragm valve.

A similar controllable diaphragm valve is known from U.S. Pat. No. 3,826,255. In general, a diaphragm valve in accordance with the invention is used in mechanical respiratory systems. Such a system comprises a valve casing enclosing a valve chamber. During an exhalation, the gases exhaled by a patient are directed through a gas inlet and a gas outlet of this chamber. During an inhalation, however, the diaphragm closes the gas inlet, thereby preventing the breathing gas being inhaled from flowing out. The closing is effected by the excess pressure produced in the control chamber above the diaphragm.

U.S. Pat. No. 3,826,255 discloses an exhaling valve comprising a cylindrical valve chamber, a gas inlet leading into the chamber to terminate in a valve seat, and a gas outlet. Extending opposite the valve seat is a diaphragm which can be sealingly applied against the valve seat. The diaphragm bounds a control chamber separate from the valve chamber. The diaphragm is held in place by a cover forming the other walls of the control chamber. Gas connections provided in the cover connect the control chamber to the controlling gas pressure source. The above exhaling valve is provided in German Pat. No. 29 47 363. This prior art valve comprises, centrally in the cover, a gas inlet connection for introducing gas into the control chamber and thus controlling the pressure to which the diaphragm is exposed.

To control the diaphragm in these prior art valves, a special control gas equipment is needed involving an additional risk of malfunction.

SUMMARY OF THE INVENTION

The present invention is directed to a pressure controlled diaphragm valve for respirators, which is incorporated in the respiratory system in a way permitting a direct control.

Accordingly the invention provides a control for use by a patient with a respirator which comprises a valve housing having an interior valve chamber with a gas inlet extending into the interior valve chamber and terminating in an annular valve seat which is closable by a diaphragm. Also connected into the valve chamber is a gas outlet, and the housing has a control chamber on the opposite side of the diaphragm from the valve chamber. A connection for the anaesthetic ventilator is connected into the control chamber and a connection connectable to the patient or to a valve supplying fresh gas is connected into the control chamber. The gas connection has a orifice plate therein which defines a reduced area in the connection which during the ventilation of the patient produces a pressure in the control chamber which is lower or higher than the pressure in the valve chamber so that the diaphragm may open or close to permit or to prevent exhaled gas to pass through the valve chamber to the gas outlet.

Accordingly it is an object of the invention to provide an improved control for use with respirators which when incorporated in the respiratory system provides a direct control without requiring further instrumentation.

A further object of the invention is to provide a control for respirators wherein the control of a diaphragm valve is effected by producing a reduced or increased pressure in the control chamber during the ventilation of the patient which permits or prevents the exhaled gas to move into the valve inlet chamber and pass off through a gas outlet.

A further object of the invention is to provide a control for a respirator which is simple in design rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the drawing:

The only FIGURE of the drawings is a sectional view of a control valve for a respirator constructed in accordance with the invention.

DESCRIPTION OF THE PREFERRED EMBODIMENT

Referring to the drawing in particular the invention embodied therein comprises a control for use by a patient with a respirator which comprises a valve housing 1 having an interior valve chamber 2. A gas inlet 5 extends into the interior valve chamber 2 and terminates in an annular valve seat 6 which is closable by a diaphragm 13. A gas outlet 7 is connected into the valve chamber 2. The housing 1 also has a control chamber 4 on the opposite side of the diaphragm 13 from the valve chamber 2. A connection 8 to an anaesthetic ventilator 20 extends into the control chamber 4. A connection 9 is connected to the patient 22 or alternatively to the fresh mixed gas supply 24 connected into the control chamber 4. Alternating with the breathing frequency the gas connection 9 is also used as an inlet for fresh mixed gas while filling the bellows 26 of the anaesthetic ventilator. The gas connection 9 has an orifice plate 10 therein defining a reduced area in the gas connection 9 wich during use by the patient produces a pressure in the control chamber 4 which is lower or higher than the pressure in the valve chamber 2. This permits or prevents the opening of the diaphragm to permit or prevent exhaled gas to pass through the gas inlet 5 to the valve chamber 2 and discharge out through the gas outlet 7.

The controllable diaphragm valve comprises a substantially cylindrical casing or housing 1 enclosing valve chamber 2, and a control chamber 4.

The ratio of the inside diameter 11 of gas outlet connection 9 to the diameter 12 of the orifice is 2:1.

The two chambers 2 and 4 are separated from each other by diaphragm 13. Under a positive differential pressure in the control chamber 4 relative to the pressure in valve chamber 2, diaphragm 13 applies against valve seat 6 of gas inlet 5. The valve has two positions:

(a) closed and (b) open.

In the closed position (a):

The inhaled gas from the anaesthetic ventilator flows through gas inlet connection 8, control chamber 4, orifice plate 10, and gas connection 9, to the patient. During this phase, the exhalation conduit including gas inlet 5 with valve seat 6 is closed by diaphragm 13. The closing pressure to which diaphragm 13 is exposed is the differential pressure between the higher pressure in control chamber 4 and the pressure in valve chamber 2, which is produced by the throttling effect of orifice plate 10 on the breathing gas flow therethrough.

In the open position (b):

While filling the bellows of the anaesthetic ventilator with fresh mixed gas through gas connection 9, control chamber 4 and connection 8 a negative differential pressure is produced in that chamber, again due to the throttling effect of orifice plate 10. Diaphragm 13 disengages from valve seat 6. The exhalation conduit from the patient through gas inlet 5, valve chamber 2 and gas outlet 7 is open.

In a respiratory system, the control of the diaphragm valve must be unconditionally reliable. Therefore, available forces must be utilized, without additional instrumentation.

In the inventive diaphragm valve, the breathing gas flows through a control chamber 4 which is separated by the diaphragm 13 from a valve chamber 2. During the inhalation, the diaphragm is exposed to a positive differential pressure from the control chamber 4, which is produced by the throttling effect of the orifice plate 10 in the gas outlet 9 and this closes the gas inlet 5 leading to the valve chamber 2. During the exhalation, the diaphragm 13 is exposed to a negative differential pressure and clears the exhalation gas flow through the valve chamber 2 to the gas outlet 7.

An advantageous feature of the invention is, particularly, that the breathing gas flow to and from the respirator is utilized for obtaining a safe closing pressure i.e. a pressure by which the diaphragm is sealingly applied against the valve seat of the exhalation gas connection. Due to the throttling effect of the orifice plate provided in the outlet of the control chamber, a surge pressure builds up resulting in a positive differential pressure, thus increased pressure, in the control chamber, closing the valve.

A preferred ratio of the inside diameter of the outlet from the control chamber to the orifice diameter of the plate is 2:1. Such a ratio results in best pressure conditions for particularly sensitive controls.

While a specific embodiment of the invention has been shown and described in detail to illustrate the application of the principles of the invention, it will be understood that the invention may be embodied otherwise without departing from such principles.

What is claimed is:

1. A control for use by a patient with a respirator, comprising a valve housing (1) having an interior valve chamber (2), an exhaled gas inlet (5) extending into said interior valve chamber and terminating in an annular valve seat (6), said valve chamber extending around said valve seat, a diaphragm (13) means having one side engagable with and disengagable from said annular valve seat to open and close said exhaled gas inlet to said valve chamber, an exhaled gas outlet (7) connected to said valve chamber for receiving exhaled gas from said exhaled gas inlet when said diaphragm means is disengaged from said valve seat, said housing having a control chamber 4 bounded by an opposite side of said diaphragm means which is opposite from said valve seat, said diaphragm means separating said control chamber from said valve chamber, a first connection (8) to an anesthetic ventilator and bellows connected to said control chamber for supplying anesthetic gas to said control chamber and for receiving fresh mixed gas from said control chamber, a second connection (9) connected to said control chamber for supplying fresh mixed gas to said control chamber and for receiving gas from said control chamber, said second connection being adapted for connection to a patient for receiving the anesthetic gas, said second connection having an orifice plate (10) therein defining a reduced area passage in said second connection so that, during an inhalation phase, the patient receives anesthetic gas from the first connection and from the control chamber to produce a higher pressure in said control chamber than in said valve chamber to cause said diaphragm means to engage against said annular seat to close said exhaled gas inlet from said exhaled gas outlet, and during an exhalation phase, fresh mixed gas is supplied through said second connection and through said orifice plate into said control chamber and through said first connection to fill the bellows, said orifice plate causing pressure in said control chamber to be less than pressure in said valve chamber to disengage said diaphragm means from said annular valve seat to open said exhaled gas inlet with respect to said exhaled gas outlet.

2. A control for a patient with a respirator according to claim 1 wherein said second connection has a diameter which is in a ratio of 2:1, to the diameter of the reduced area passage defined by said orifice plate and through which anesthetic gas and fresh mixed gas pass to produce differential pressures between said control chamber and said valve chamber.

3. A control for a patient with a respirator according to claim 1, including an anesthetic ventilator (20) having a bellows (26) and being connected to said first connection (8), and a fresh mixed gas supply (24) connected to said second connection (9).

* * * * *